United States Patent [19]
Yoshida et al.

[11] Patent Number: 5,518,903
[45] Date of Patent: May 21, 1996

[54] PROCESS FOR PRODUCING OPTICALLY ACTIVE 3-AMINOBUTANOIC ACID AND THE ESTER INTERMEDIATES

[75] Inventors: Naoyuki Yoshida; Teruyo Sugiura; Yasuyuki Koizumi, all of Ichihara, Japan

[73] Assignee: Chisso Corporation, Osaka, Japan

[21] Appl. No.: 289,031

[22] Filed: Aug. 11, 1994

[30] Foreign Application Priority Data

Aug. 13, 1993 [JP] Japan ................................. 5-237125

[51] Int. Cl.$^6$ .............................. C12P 41/00; C12N 9/14; C12N 9/16
[52] U.S. Cl. ................... 435/106; 435/195; 435/196; 435/197; 435/198; 435/280
[58] Field of Search .................................. 435/106, 195, 435/196, 197, 280, 198

[56] References Cited

FOREIGN PATENT DOCUMENTS 0513810  11/1992  European Pat. Off. .

OTHER PUBLICATIONS

Davis et al., Tetrahedron: Asymmetry, vol. 2, No. 3, pp. 183–1986 (1991).
Lubell et al., Tetrahedron: Asymmetry, vol. 2, No. 7, pp. 543–554 (1991).
Juaristi et al., J. Org. Chem., vol. 57, No. 8 (1992) pp. 2396–2398.
Hunt et al., J. Biol. Chem., vol. 127, pp. 727–735 (1939).
Fischer et al., Liebigs Ann. Chem., vol. 383, pp. 337–363 (1911).
Rossi et al., Experientia, vol. 33, pp. 1557–1559 (1977).
Gmeiner, Liebigs Ann. Chem., pp. 501–502 (1991).
Jefford et al., Tetrahedron Letters, vol. 34, No. 7, pp. 1111–1114 (1993).
Estermann et al., Helvetica Chemica Acta., vol. 71, pp. 1824–1839 (1988).

*Primary Examiner*—Herbert J. Lilling
*Attorney, Agent, or Firm*—Wenderoth, Lind & Ponack

[57] ABSTRACT

The present invention provides a process for producing optically active 3-aminobutanoic acid characterized in that it comprises an asymmetrically hydrolyzing racemic ester of 3-substituted aminobutanoic acid in the presence of a hydrolase, obtaining an optically active ester of 3-substituted aminobutanoic acid and an optically active 3-substituted aminobutanoic acid of an enantiomer of the ester, and treating the above ester represented by the formula (II):

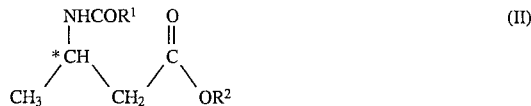

to remove the protecting group. In addition, the new ester intermediates represented by the above formula (II) are provided.

6 Claims, No Drawings

PROCESS FOR PRODUCING OPTICALLY ACTIVE 3-AMINOBUTANOIC ACID AND THE ESTER INTERMEDIATES

BACKGROUND OF THE INVENTION

1. Field of the Invention

The present invention relates to a process for producing optically active 3-aminobutanoic acid and ester intermediates which are produced in the above process. More particularly, the present invention relates to a process for producing optically active 3-aminobutanoic acids, which are useful for industrial fields, in the presence of a hydrolase, and new ester intermediates produced in the process.

2. Description of the Prior Art

Lately, it becomes important to synthesize physiologically active substances as optically active compounds. In a physiologically active substance having several kinds of optical isomers, these isomers often show difference in activity. Among these isomers, one isomer has strong activity and the other isomers show weak activity or undesired toxicity. Accordingly, when the physiologically active substances are synthesized as medical supplies, it is desired to selectively synthesize preferable optical isomers not only to develop full physiological activity but also in safety.

Optically active 3-amino butanoic acid is widely useful as intermediates for synthesizing physiologically active materials. For example, the above compound can be used as a starting material of peptide-like compounds having a function by which platelet aggregation is inhibited (R. B. Garland et al., EP 513810). Many production examples of optically active 3-aminobutanoic acid have been reported. For instance, as methods using asymmetric synthesis, 1) an asymmetric Michael method for adding an optically active lithium amide derivative to crotonic acid ester (S. G. Davies et al., Tetrahedron: Asymmetry, 2, 183 (1991)), and 2) a method for asymmetric reduction of 3-acylaminocrotonic acid ester with a BINAP-rhodium (II) complex (W. D. Lubell et al., Tetrahedron: Asymmetry, 2, 543 (1991) are known. As methods for using optical resolution, there are 3) a Michael method for adding optically active phenylethyl amine to crotonic acid ester to separate two obtained diastereomers by chromatography (E. Juaristi et al., J. Org. Chem., 57, 2396 (1992), and 4) a method of optical resolution by recrystalization of a diastereomer salt derived from racemic 3-aminobutanoic acid (M. Hunt et al., J. Biol. Chem., 127, 727 (1939), E. Fischer et al., Liebigs Ann. Chem., 383, 337 (1911)). As methods for using a biocatalyst, 5) a method of optical resolution of 3-acylaminobutanoic acid with benzylpenicillin acylase (D. Rossi et al., Experientia, 33, 1557 (1977) is known. Further, as a method for converting a commercially available optically active compound, which is used as a starting material, to optically active 3-aminobutanoic acid, there is 6) a method using L-aspartic acid (P. Gmeiner, Liebigs Ann. Chem., 1991, 501, C. W. Jefford et al., Tetrahedron Lett., 34, 1111 (1993)). However, method 1 ) needs a low temperature condition of −78° C. Method 2) needs an expensive reagent and a special reaction equipment. Method 3) needs a chromatograph for separating isomers. Method 4) needs repeated recrystallization to obtain high optical purity. In method 5), it is difficult to obtain the enzyme. In method 6), there are many troublesome steps.

As described above, these conventional methods have problems of industrial level operation, unsatisfactorily. As an industrially useful method, there is an enzyme method. For example, a method for optical resolution of α-amino acid with a hydrolase, more particularly, a method for asymmetrically hydrolyzing an ester group to synthesize optically active α-amino acid is known. However, a method for synthesizing β-amino acid (3-amino carboxylic acid) is quite unknown except a method reported by Zeebach (Helvetica Chimica Acta., 71, 1824 (1988)). The latter method has problems that both chemical and optical yield are very low (30% and 68%ee, respectively) and recrystallization should be repeated to enhance the optical purity.

SUMMARY OF THE INVENTION

The object of the present invention is to overcome the above problems of the prior art, to provide a method for producing optically active 3-aminobutanoic acid in high yield by simple operation and to provide new ester intermediates which are produced in the method.

The inventors of the present invention carried out research to achieve the object, and they found a process for producing optically active 3-substituted aminobutanoic acid from ester of racemic 3-substituted aminobutanoic acid. Further, they found that optically active ester compounds of 3-substituted aminobutanoic acid were new precursors appropriate to produce the optically active 3-substituted aminobutanoic acid, and the present invention has been achieved.

The present invention is firstly characterized in a process for producing optically active 3-aminobutanoic acid comprising asymmetrically hydrolyzing racemic ester of 3-substituted aminobutanoic acid represented by the general formula:

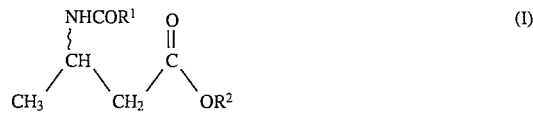

(I)

wherein $R^1$ is alkyl of 1–10 carbon atoms, aryl, aralkyl, alkoxy of 1–10 carbon atoms, aryloxy or aralkyloxy, $R^2$ is alkyl of 1–20 carbon atoms, aryl or aralkyl, in the presence of a hydrolase, obtaining optically active ester of 3-substituted aminobutanoic acid represented by the general formula:

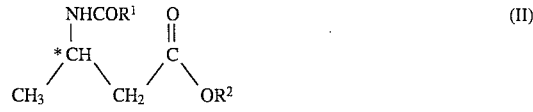

(II)

wherein $R^1$ and $R^2$ are as indicated above, and * shows an asymmetric carbon, and optically active 3-substituted aminobutanoic acid represented by the general formula:

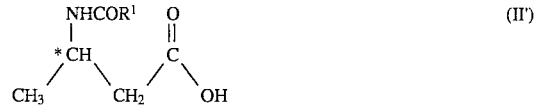

(II')

wherein $R^1$ and * are as indicated above, which is an enantiomer of the above ester, and treating the above ester (II) to remove the protecting group.

The present invention is secondly characterized in an optically active ester of 3-substituted aminobutanoic acid which is represented by the general formula:

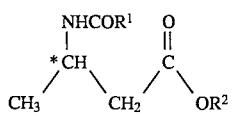

(II)

wherein $R^1$ is alkyl of 1–10 carbon atoms, aryl, aralkyl, alkoxy of 1–10 carbon atoms, aryloxy or aralkyloxy, $R^2$ is alkyl of 1–20 carbon atoms, aryl or aralkyl, and * shows an asymmetric carbon.

As preferable examples of $R^1$ and $R^2$ of the above formulas, methyl, ethyl, propyl, isopropyl and butyl in case of alkyl; phenyl, methoxyphenyl, chlorophenyl and bromophenyl in case of aryl; and benzyl, methoxybenzyl, chlorobenzyl and bromobenzyl in case of aralkyl can be exemplified. As preferable examples of $R^1$, methoxy, ethoxy, propyloxy, isopropyloxy, butyloxy and tertbutyloxy in case of alkoxy; phenoxy, methoxyphenyloxy, chlorophenyloxy and bromophenyloxy in case of aryloxy; and benzyloxy, methoxybenzyloxy, chlorobenzyloxy and bromobenzyloxy in case of aralkyloxy can be exemplified.

The following description illustrates the present invention more specifically. Optically active 3-aminobutanoic acid (IV) can be prepared by the following steps.

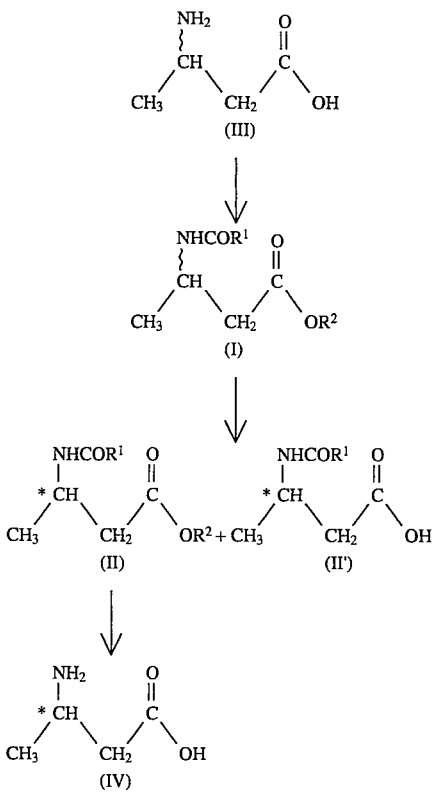

wherein $R^1$, $R^2$ and * are as indicated above.

Racemic ester of 3-substituted aminobutanoic acid (I) which is used as a starting material in the present invention can be easily prepared by successively protecting an amino group and a carboxyl group of racemic 3-aminobutanoic acid (III) in the usual way. For example, by using a Schotten-Baumann Method, racemic 3-aminobutanoic acid is reacted with di-tert-butyldicarbonate in a mixture of an aqueous sodium hydroxide solution and 1,3-dioxane to convert the amino group of the racemate to a tert-butoxycarbonyl amino group, and the carboxyl group is changed to a benzyl ester with benzyl bromide in dimethyl formamide in the presence of potassium bicarbonate, and benzyl ester of 3-tert-butoxycarbonylamino butanoic acid can be obtained.

Using ester of 3-substituted aminobutanoic acid (I) obtained by such a method, the first step of the process of the present invention can be conducted. Namely, by asymmetrically hydrolyzing the ester group of the compound represented by the formula (I), optically active ester of 3-substituted aminobutanoic acid (II) of a new ester intermediate and optically active 3-substituted aminobutanoic acid (II') of an enantiomer of the above ester can be easily obtained.

$R^2$ of ester of 3-substituted aminobutanoic acid (I) is as mentioned above. When $R^2$ is benzyl, optically active ester of 3-substituted aminobutanoic acid having high optical purity can be obtained especially in a high yield.

As the reaction conditions of the first step, the reaction temperature is suitably 10° C. to 100° C., and preferably 20° C. to 45° C. The reaction time is suitably one to 1000 hours, and preferably 20 to 300 hours. The pH of the reaction system can be dependent on the optimum pH of the hydrolytic enzyme, and it is preferably maintained in the range of 4 to 10. A buffer solution can be suitably used to adjust the pH value.

The reaction is generally conducted in the presence of solvent. As the solvent, organic solvent, which can be easily mixed with the above-mentioned buffer, such as acetone, dimethyl formamide, dimethyl sulfoxide, alcohols such as methanol can be exemplified.

As the hydrolase, esterase produced from microorganisms or esterase from animals can be suitably used. When the former esterase is used, the esterase having hydrolysis ability can be used without limiting the species of the microorganisms. As such microorganisms, the genera Pseudomonas, Chromobacterium, Arthrobacter, Acromobacter, Alcaligenes, Aspergillus, Candida, Mucor, Rhizopus, etc, can be exemplified.

The following table shows commercially available esterases.

TABLE 1

| Trade name | Origin | Seller or Maker |
|---|---|---|
| Lipase PS | Pseudomonas fluorescens | Amano Pharmaceutical Co., Ltd. |
| Lipase CES | Pseudomonas sp | Amano Pharmaceutical Co., Ltd. |
| Lipase AS | Aspergillus niger | Amano Pharmaceutical Co., Ltd. |
| Lipase M | Mucor javanicus | Amano Pharmaceutical Co., Ltd. |
| Lipase CE | Humicola lanuginosa | Amano Pharmaceutical Co., Ltd. |
| Lipase F-AP | Rhizopus javanicus | Amano Pharmaceutical Co., Ltd. |
| Lipase II | Porcine pancreas | Sigma Chemical Co., Ltd. |
| Lipase VII | Candida cylindracea | " |
| Esterase | pig liver | " |
| Liver acetone powder | " | " |
| Lipase | Chromobacterium viscosum | Asahi Chemical Industry Co., Ltd. |
| Palatase A | Aspergillus niger | Novo Nordisk |
| Lipozyme 1M | Mucor miehei | " |
| Lipase | Rhizopus niveus | Nagase & Co., Ltd. |
| Lipase B | Pseudomonus fragi | Sapporo Breweries, Ltd. |
| Lipase | Pseudomonas sp | Toyobo Co., Ltd. |

In these esterases, esterases which are produced with microorganisms from Pseudomonas or Chromobacterium, can be preferably used.

After the asymmetric hydrolysis reaction is finished, the enzyme is removed by filtration. The reaction solution is extracted under basic conditions to obtain optically active ester of 3-substituted aminobutanoic acid (II), and then the reaction solution is extracted under acidic conditions to obtain optically active 3-substituted aminobutanoic acid which is an enantiomer of the above ester. These products can be further purified by applying conventional separating methods such as distillation, column chromatography or the like.

Then, the latter step of the production process of the present invention is shown in the following. The step is comprised removing the protective groups (—COR$^1$ and —R$^2$) of the amino group and the carboxyl group of the optically active ester of 3-substituted aminobutanoic acid (II) which is obtained in the former step. The removing treatment is generally conducted by a conventional method which is widely known. For example, to treat benzyl 3-tert-butoxycarbonylaminobutanoate which is an example of the compounds (II), the benzyl group is deprotected by hydrogenolysis in the presence of palladium hydroxide-carbon catalyst, and then the tert-butoxycarbonyl group is deprotected with formic acid. The process is suitably attained by the above step.

Further, the optically active ester of 3-substituted aminobutanoic acid (II) was prepared for the first time by the inventors of the present invention. As these compounds,
(+)-methyl 3-acetylaminobutanoate,
(+)-ethyl 3-acetylaminobutanoate,
(+)-isopropyl 3-acetylaminobutanoate,
(+)-tert-butyl 3-acetylaminobutanoate,
(+)-phenyl 3-acetylaminobutanoate,
(+)-benzyl 3-acetylaminobutanoate,
(+)-ethyl 3-benzoylaminobutanoate,
(+)-isopropyl 3-benzoylaminobutanoate,
(+)-tert-butyl 3-benzoylaminobutanoate,
(+)-phenyl 3-benzoylaminobutanoate,
(+)-benzyl 3-benzoylaminobutanoate,
(+)-methyl 3-methoxycarbonylaminobutanoate,
(+)-ethyl 3-methoxycarbonylaminobutanoate,
(+)-isopropyl 3-methoxycarbonylaminobutanoate,
(+)-tert-butyl 3-methoxycarbonylaminobutanoate,
(+)-phenyl 3-methoxycarbonylaminobutanoate,
(+)-benzyl 3-methoxycarbonylaminobutanoate,
(+)-methyl 3-tert-butoxycarbonylaminobutanoate,
(+)-ethyl 3-tert-butoxycarbonylaminobutanoate,
(+)-isopropyl 3-tert-butoxycarbonylaminobutanoate,
(+)-tert-butyl 3-tert-butoxycarbonylaminobutanoate,
(+)-phenyl 3-tert-butoxycarbonylaminobutanoate,
(+)-benzyl 3-tert-butoxycarbonylaminobutanoate,
(+)-methyl 3-benzyloxycarbonylaminobutanoate,
(+)-ethyl 3-benzyloxycarbonylaminobutanoate,
(+)-isopropyl 3-benzyloxycarbonylaminobutanoate,
(+)-tert-butyl 3-benzyloxycarbonylaminobutanoate,
(+)-phenyl 3-benzyloxycarbonylaminobutanoate,
(+)-benzyl 3-benzyloxycarbonylaminobutanoate,
(−)-methyl 3-acetylaminobutanoate,
(−)-ethyl 3-acetylaminobutanoate,
(−)-isopropyl 3-acetylaminobutanoate,
(−)-tert-butyl 3-acetylaminobutanoate,
(−)-phenyl 3-acetylaminobutanoate,
(−)-benzyl 3-acetylaminobutanoate,
(−)-ethyl 3-benzoylaminobutanoate,
(−)-isopropyl 3-benzoylaminobutanoate,
(−)-tert-butyl 3-benzoylaminobutanoate,
(−)-phenyl 3-benzoylaminobutanoate,
(−)-benzyl 3-benzoylaminobutanoate,
(−)-methyl 3-methoxycarbonylaminobutanoate,
(−)-ethyl 3-methoxycarbonylaminobutanoate,
(−)-isopropyl 3-methoxycarbonylaminobutanoate,
(−)-tert-butyl 3-methoxycarbonylaminobutanoate,
(−)-phenyl 3-methoxycarbonylaminobutanoate,
(−)-benzyl 3-methoxycarbonylaminobutanoate,
(−)-methyl 3-tert-butoxycarbonylaminobutanoate,
(−)-ethyl 3-tert-butoxycarbonylaminobutanoate,
(−)-isopropyl 3-tert-butoxycarbonylaminobutanoate,
(−)-tert-butyl 3-tert-butoxycarbonylaminobutanoate,
(−)-phenyl 3-tert-butoxycarbonylaminobutanoate,
(−)-benzyl 3-tert-butoxycarbonylaminobutanoate,
(−)-methyl 3-benzyloxycarbonylaminobutanoate,
(−)-ethyl 3-benzyloxycarbonylaminobutanoate,
(−)-isopropyl 3-benzyloxycarbonylaminobutanoate,
(−)-tert-butyl 3-benzyloxycarbonylaminobutanoate,
(−)-phenyl 3-benzyloxycarbonylaminobutanoate,
(−)-benzyl 3-benzyloxycarbonylaminobutanoate,
and the like can be exemplified.

The merits of the present invention are as follows. The optically active esters of 3-substituted aminobutanoic acid which are new ester intermediates can be provided. In addition, the optically active 3-aminobutanoic acid useful as a starting material for synthesizing many physiologically active materials can be obtained by simple operation by using the intermediates, and the product having high optical purity can be obtained in high yield.

DESCRIPTION OF THE PREFERRED EMBODIMENTS

The following examples illustrate the present invention more specifically, but these are not intended as a definition of the limits of the invention.

Reference Example 1

Production of (±)-methyl 3-tert-butoxycarbonylaminobutanoate (in formula (I), R$^1$=tert-butoxy, R$^2$=methyl)

To a mixture of (±)-3-aminobutanoic acid 10.0 g (97.0 mmol), sodium hydroxide 4.4 g (106 mmol), dioxane 100 ml and water 200 ml, di-tert-butyldicarbonate 23.5 g (108 mmol) was added dropwise on ice cooling. The mixture was stirred for 24 hours at room temperature. After the organic layer was concentrated, potassium hydrogen sulfate 17.3 g (dissolved in water 85 ml) was added on ice cooling. The mixture was extracted with ethyl acetate, and the extract was washed with a saturated solution of sodium chloride. The organic layer was dried over anhydrous magnesium sulfate, filtered and concentrated to obtain crude 3-tert-butoxycarbonylaminobutanoic acid 17.6 g. The crude product 17.6 g (86.6 mmol) was dissolved in dimethylformamide 130 ml. After adding potassium hydrogen carbonate 13.0 g (130 mmol) and methyl iodide 27.3 g (192 mmol), the mixture was stirred for 24 hours at room temperature. The reaction mixture was added to ice water, and the mixture was extracted with ethyl acetate. The extract was washed with water, and a saturated solution of sodium chloride. The organic layer was dried over anhydrous magnesium sulfate, filtered and concentrated to obtain crude methyl 3-tert-butoxycarbonylaminobutanoate 18.8 g. The product was purified by silica gel column chromatography (heptane:ethyl acetate=5:1) to obtain (±)-methyl 3-tert-butoxycarbonylaminobutanoate 16.5 g (76.0 mmol). Yield 78%.

EXAMPLE 1

Production of (+)-3-aminobutanoic acid and (−)-3-tert-butoxycarbonylaminobutanoic acid Step 1

A mixture of (±)-methyl 3-tert-butoxycarbonylaminobutanoate 2.01 g (9.26 mmol), Lipase (manufactured by Asahi Chemical Industry Co., Ltd.) 1.02 g and a $^1/_{15}$M phosphate buffer solution (pH 7.0) 50 ml was stirred for 11 days at room temperature. After Lipase was filtered off, the filtrate was extracted with diethyl ether. The extract was washed with a 1N aqueous solution of sodium hydroxide and a saturated aqueous solution of sodium chloride, successively. After drying over anhydrous magnesium sulfate, the organic layer was filtered and concentrated to obtain crude (+)-methyl 3-tert-butoxycarbonylaminobutanoate 789 mg.

$[\alpha]_D^{27}$+16.4° (c 1.193, CHCl$_3$)

Since a specific rotation of (+)-methyl 3-tert-butoxycarbonylaminobutanoate derived from optically pure (+)-3-aminobutanoic acid is $[\alpha]_D^{25}$+22.2° (c 1.199, CHCl$_3$), optical purity of the product is about 74%ee.

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (−)-3-tert-butoxycarbonylaminobutanoic acid 1.24 g.

Step 2

(+)-methyl 3-tert-butoxycarbonylaminobutanoate 502 mg (2.31 mmol) was dissolved in methanol 5 ml. Sodium hydroxide 200 mg (4.80 mmol) was added on ice cooling, the mixture was stirred for 22 hours at room temperature. The reaction mixture was adjusted to pH 3 with dilute hydrochloric acid and extracted with ethyl acetate. The extract was washed with a saturated aqueous solution of sodium chloride, dried over magnesium sulfate, filtered and concentrated. The residue was dissolved in formic acid 2 ml. The solution was stirred for 60 hours at room temperature, and concentrated to obtain crude (+)-3-aminobutanoic acid 340 mg.

EXAMPLE 2

Production of (+)-methyl 3-tert-butoxycarbonylaminobutanoate and (−)-3-tert-butoxycarbonylaminobutanoic acid A mixture of (±)-methyl 3-tert-butoxycarbonylaminobutanoate 512 mg (2.34 mmol), Lipase PS (manufactured by Amano Pharmaceutical Co., Ltd.) 505 mg and a 1/15M phosphate buffer solution (pH 7.0) 20 ml was stirred for 9 days at room temperature. After the esterase was filtered off, the filtrate was extracted with ethyl acetate. The extract was washed with a 1N aqueous solution of sodium hydroxide and a saturated aqueous solution of sodium chloride, successively. After drying over anhydrous magnesium sulfate, the organic layer was filtered and concentrated to obtain crude (+)-methyl 3-tert-butoxycarbonylaminobutanoate 151 mg.

$[\alpha]_D^{23}$+14.7° (c 1.549, CHCl$_3$)

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (−)-3-tert-butoxycarbonylaminobutanoic acid 333 mg.

EXAMPLE 3

Production of (+)-methyl 3-tert-butoxycarbonylaminobutanoate and (−)-3-tert-butoxycarbonylaminobutanoic acid A mixture of (±)-methyl 3-butoxycarbonylaminobutanoate 509 mg (2.34 mmol), Lipase (manufactured by Asahi Chemical Industry Co., Ltd.) 253 mg, a 1/15M phosphate buffer solution (pH 7.0) 10 ml and acetone 1 ml was stirred for 8 days at room temperature. After the esterase was filtered off, the filtrate was extracted with ethyl acetate. The extract was washed with a 1N aqueous solution of sodium hydroxide and a saturated aqueous solution of sodium chloride, successively. After drying over anhydrous magnesium sulfate, the organic layer was filtered and concentrated to obtain crude (+)-methyl 3-tert-butoxycarbonylaminobutanoate 310 mg.

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (−)-3-tert-butoxycarbonylaminobutanoic acid 181 mg.

$[\alpha]_D^{26}$+12.2° (c 1.019, CHCl$_3$)

Since a specific rotation of (+)-3-tert-butoxycarbonylaminobutanoic acid derived from optically pure (+)-3-aminobutanoic acid is $[\alpha]_D^{24}$+17.5° (c 1.256, CHCl$_3$), optical purity of the product is about 70%ee.

EXAMPLE 4

Production of (+)-methyl 3-tert-butoxycarbonylaminobutanoate and (−)-3-tert-butoxycarbonylaminobutanoic acid A mixture of (±)-methyl 3-tert-butoxycarbonylaminobutanoate 500 mg (2.30 mmol), Lipase PS (manufactured by Amano Pharmaceutical Co., Ltd.) 250 mg and a ½M phosphate buffer solution (pH 7.0) 2.5 ml was stirred for 6 days at room temperature. After the esterase was filtered off, the filtrate was extracted with ethyl acetate. The extract was washed with a 1N aqueous solution of sodium hydroxide and a saturated aqueous solution of sodium chloride, successively. After drying over anhydrous magnesium sulfate, the organic layer was filtered and concentrated to obtain crude (+)-methyl 3-tert-butoxycarbonylaminobutanoate 284 mg.

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (−)-3-tert-butoxycarbonylaminobutanoic acid 203 mg.

$[\alpha]_D^{23}$−10.4° (c 1.041, CHCl$_3$)

EXAMPLE 5

Production of (−)-methyl 3-tert-butoxycarbonylaminobutanoate and (+)-3-tert-butoxycarbonylaminobutanoic acid A mixture of (±)-methyl 3-tert-butoxycarbonylaminobutanoate 506 mg (2.33 mmol), Esterase (PLE: manufactured by Sigma Chemical Co., Ltd.) 250 mg and a 1/15M phosphate buffer solution (pH 7.0) 40 ml was stirred for 3 days at room temperature. After the esterase was filtered off, the filtrate was extracted with ethyl acetate. The extract was washed with a 1N aqueous solution of sodium hydroxide and a saturated aqueous solution of sodium chloride successively. After drying over anhydrous magnesium sulfate, the organic layer was filtered and concentrated to obtain crude (−)-methyl 3-tert-butoxycarbonylaminobutanoate 117 mg.

$[\alpha]_D^{27}$−9.3° (c 1.100, CHCl$_3$)

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (+)-3-tert-butoxycarbonylaminobutanoic acid 360 mg.

EXAMPLE 6

Production of (−)-methyl 3-tert-butoxycarbonylaminobutanoate and (+)-3-tert-butoxycarbonylaminobutanoic acid A mixture of (±)-mehtyl 3-tert-butoxycarbonylaminobutanoate 510 mg (2.35 mmol), Liver acetone powder (manufactured by Sigma Chemical Co., Ltd.) 252 mg, $\frac{1}{15}$M phosphate buffer solution (pH 7.0) 10 ml and acetone 1 ml was stirred for 7 days at room temperature. After the esterase was filtered off, the filtrate was extracted with ethyl acetate. The extract was washed with a 1N aqueous solution of sodium hydroxide and a saturated aqueous solution of sodium chloride, successively. After drying over anhydrous magnesium sulfate, the organic layer was filtered and concentrated to obtain crude (−)-methyl 3-tert-butoxycarbonylaminobutanoate 306 mg.

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (+)-3-tert-butoxycarbonylaminobutanoic acid 168 mg.

$[\alpha]_D^{24}$ +5.6° (c 1.168, CHCl$_3$)

Reference Example 2

Production of (±)-butyl 3-tert-butoxycarbonylaminobutanoate (in formula (I), R$^1$=tert-butoxy, R$^2$=butyl)

To a mixture of (±)-3-aminobutanoic acid 10.0 g (97.0 mmol), sodium hydroxide 4.5 g (107 mmol), dioxane 100 ml and water 200 ml, di-tert-butyldicarbonate 24.2 g (111 mmol) was added dropwise on ice cooling. The mixture was stirred for 19.5 hours at room temperature. After the organic layer was concentrated, potassium hydrogen sulfate 18.4 g (dissolved in water 90 ml) was added on ice cooling. The mixture was extracted with ethyl acetate, and the extract was washed with a saturated solution of sodium chloride. The organic layer was dried over anhydrous magnesium sulfate, filtered and concentrated to obtain crude 3-tert-butoxycarbonylaminobutanoic acid 17.0 g. The crude product 14.3 g (70.6 mmol) was dissolved in dimethylformamide 150 ml. After adding potassium hydrogen carbonate 14.9 g (149mmol) and butyl iodide 30.3 g (165 mmol), the mixture was stirred for 26 hours at room temperature. The reaction mixture was added to ice water, and the mixture was extracted with ethyl acetate. The extract was washed with water and a saturated solution of sodium chloride, successively. The organic layer was dried over anhydrous magnesium sulfate, filtered and concentrated to obtain crude butyl 3-tert-butoxycarbonylaminobutanoate 18.5 g. The product was purified by silica gel column chromatography (heptane:ethyl acetate= 10:1) to obtain (±)-butyl 3-tert-butoxycarbonylaminobutanoate 15.0 g (57.8 mmol). Yield 71%.

EXAMPLE 7

Production of (+)-butyl 3-tert-butoxycarbonylaminobutanoate and (−)-3-tert-butoxycarbonylaminobutanoic acid A mixture of (±)-butyl 3-tert-butoxycarbonylaminobutanoate 307 mg (1.18 mmol), Lipase (manufactured by Asahi Chemical Industry Co., Ltd.) 155 mg and a $\frac{1}{15}$M phosphate buffer solution (pH 7.0) 6 ml was stirred for 8 days at room temperature. After the esterase was filtered off, the filtrate was extracted with ethyl acetate. The extract was washed with a 1N aqueous solution of sodium hydroxide and a saturated aqueous solution of sodium chloride, successively. After drying over anhydrous magnesium sulfate, the organic layer was filtered and concentrated to obtain crude (+)-butyl 3-tert-butoxycarbonylaminobutanoate 160 mg.

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (−)-3-tert-butoxycarbonylaminobutanoic acid 89 mg.

$[\alpha]_D^{24}$ −8.0° (c 1.006, CHCl$_3$)

EXAMPLE 8

Production of (+)-butyl 3-tert-butoxycarbonylaminobutanoate and (−)-3-tert-butoxycarbonylaminobutanoic acid A mixture of (±)-butyl 3-tert-butoxycarbonylaminobutanoate 313 mg (1.21 mmol), Lipase PS (manufactured by Amano Pharmaceutical Co., Ltd.) 151 mg and a $\frac{1}{15}$M phosphate buffer solution (pH 7.0) 6 ml was stirred for 7 days at room temperature. After the esterase was filtered the filtrate was extracted with ethyl acetate. The extract was washed with a 1N aqueous solution of sodium hydroxide and a saturated aqueous solution of sodium chloride, successively. After drying over anhydrous magnesium sulfate, the organic solution was filtered and concentrated to obtain crude (+)-butyl 3-tert-butoxycarbonylaminobutanoate 193 mg.

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (−)-3-tert-butoxycarbonylaminobutanoic acid 101 mg.

$[\alpha]_D^{26}$ −10.7° (c 1.026, CHCl$_3$)

Reference Example 3

Production of (±)-benzyl 3-tert-butoxycarbonylaminobutanoate (in formula (I), R$^1$=tert-butoxy, R$^2$= benzyl)

To a mixture of (±)-3-aminobutanoic acid 10.0 g (97.1 mmol), sodium hydroxide 4.5 g (107 mmol), dioxane 100 ml and water 200 ml, di-tert-butyldicarbonate 23.9 g (109 mmol) was added dropwise on ice cooling. The mixture was stirred for 22.5 hours at room temperature. After the organic layer was concentrated, potassium hydrogen sulfate 19.0 g (dissolved in water 100 ml) was added on ice cooling. The mixture was extracted with ethyl acetate, and the extract was washed with a saturated solution of sodium chloride. The organic layer was dried over anhydrous magnesium sulfate, filtered and concentrated to obtain crude 3-tert-butoxycarbonylaminobutanoic acid 14.1 g.

The crude product 10.0 g (49.3 mmol) was dissolved in dimethylformamide 75 ml. After adding potassium hydrogen carbonate 7.6 g (76.2 mmol) and benzyl bromide 17.1 g (99.9 mmol), the mixture was stirred for 46.5 hours at room temperature. The reaction mixture was added to ice water, and the mixture was extracted with ethyl acetate. The extract was washed with water and a saturated aqueous solution of sodium chloride, successively. The organic layer was dried over anhydrous magnesium sulfate, filtered and concentrated to obtain crude benzyl 3-tert-butoxycarbonylaminobutanoate 20.4 g. The product was purified by silica gel column chromatography (heptane:ethyl acetate=7:1) to obtain (±)-benzyl 3-tert-butoxycarbonylaminobutanoate 14.3 g (48.8 mmol). Yield 71%.

EXAMPLE 9

Production of (+)-3-aminobutanoic acid and (−)-3-tert-butoxycarbonylaminobutanoic acid Step 1

A mixture of (±)-benzyl 3-tert-butoxycarbonylaminobutanoate 2.02 g (6.89 mmol), Lipase (manufactured by Asahi Chemical Industry Co., Ltd.) 1.16 g and a 1/15M phosphate buffer solution (pH 7.0) 40 ml was stirred for 9 days at room temperature. After the esterase was filtered off, the mixture was extracted with diethyl ether. The extract was washed with a 1N aqueous solution of sodium hydroxide and a saturated aqueous solution of sodium chloride, successively. The organic layer was dried over anhydrous magnesium sulfate, filtered and concentrated to obtain crude benzyl 3-tert-butoxycarbonylaminobutanoate 1.32 g. The product was purified by silica gel column chromatography (heptane:ethyl acetate=10:1) to obtain (+)-benzyl 3-tert-butoxycarbonylaminobutanoate 0.94 g.

$[\alpha]_D^{26} +20.4°$ (c 1.008, CHCl$_3$)

Since a specific rotation of (+)-benzyl 3-tert-butoxycarbonylaminobutanoate derived from optically pure (+)-3-aminobutanoic acid is $[\alpha]_D^{27} +20.1°$ (c 1.092 CHCl$_3$), the compound is nearly optically pure.

On the other hand, an aqueous layer was adjusted to pH 3 with dilute hydrochloric acid and extracted with diethyl ether. The extract was washed with a saturated aqueous solution of sodium chloride, dried over anhydrous magnesium sulfate, filtered and concentrated to obtain crude (−)-3-tert-butoxycarbonylaminobutanoic acid 750 mg.

Step 2

(+)-benzyl 3-tert-butoxycarbonylaminobutanoate 500 mg (1.70 mmol) was dissolved in methanol 5 ml, 20% palladium hydroxide-carbon 106 mg was added, and the mixture was stirred for 4 hours in an atmosphere of hydrogen. The catalyst was filtered off, and the filtrate was concentrated. The residue was dissolved in formic acid 2 ml and the mixture was stirred for 60 hours at room temperature. The reaction solution was concentrated and crude (+)-3-aminobutanoic acid 250 mg was obtained.

EXAMPLE 10

Production of (+)-benzyl 3-tert-butoxycarbonylaminobutanoate and (−)-3-tert-butoxycarbonylaminobutanoic acid A mixture of (±)-benzyl 3-tert-butoxycarbonylaminobutanoate 306 mg (1.04 mmol), Lipase PS (manufactured by Amano Pharmaceutical Co., Ltd.) 155 mg and a 1/15M phosphate buffer solution (pH 7.0) 6 ml was stirred for 6 days at room temperature. After the esterase was filtered off, the filtrate was extracted with ethyl acetate. The extract was washed with a 1N aqueous solution of sodium hydroxide and a saturated aqueous solution of sodium chloride, successively. The organic layer was dried over anhydrous magnesium sulfate, filtered and concentrated to obtain crude benzyl 3-tert-butoxycarbonylaminobutanoate 230 mg. The product was purified by silica gel column chromatography (heptane:ethyl acetate=8:1) to obtain (+)-benzyl 3-tert-butoxycarbonylaminobutanoate 123 mg.

$[\alpha]_D^{25} +18.0°$ (c 1.023, CHCl$_3$)

On the other hand, an aqueous layer was adjusted to pH 3 with dilute hydrochloric acid and extracted with ethyl acetate. The extract was washed with a saturated aqueous solution of sodium chloride, dried over anhydrous magnesium sulfate, filtered and concentrated to obtain crude (−)-3-tert-butoxycarbonylaminobutanoic acid 117 mg.

We claim:

1. A process for producing optically active 3-aminobutanoic acid comprising asymmetrically hydrolyzing racemic ester of 3-substituted amino butanoic acid represented by the general formula:

$$\begin{array}{c} \text{NHCOR}^1 \quad\; \text{O} \\ | \qquad\qquad \| \\ \text{CH} \qquad\; \text{C} \\ / \;\;\; \backslash \quad / \;\;\; \backslash \\ \text{CH}_3 \quad\; \text{CH}_2 \quad\; \text{OR}^2 \end{array} \quad (I)$$

wherein R$^1$ is alkyl of 1–10 carbon atoms, aryl, aralkyl, alkoxy of 1–10 carbon atoms, aryloxy or aralkyloxy, R$^2$ is alkyl of 1–20 carbon atoms, aryl or aralkyl, in the presence of a hydrolase, obtaining optically active ester of 3-substituted aminobutanoic acid represented by the general formula:

$$\begin{array}{c} \text{NHCOR}^1 \quad\; \text{O} \\ | \qquad\qquad \| \\ \text{*CH} \qquad\; \text{C} \\ / \;\;\; \backslash \quad / \;\;\; \backslash \\ \text{CH}_3 \quad\; \text{CH}_2 \quad\; \text{OR}^2 \end{array} \quad (II)$$

wherein R$^1$ and R$^2$ are as indicated above, and * shows an asymmetric carbon, and optically active 3-substituted aminobutanoic acid represented by the general formula:

$$\begin{array}{c} \text{NHCOR}^1 \quad\; \text{O} \\ | \qquad\qquad \| \\ \text{*CH} \qquad\; \text{C} \\ / \;\;\; \backslash \quad / \;\;\; \backslash \\ \text{CH}_3 \quad\; \text{CH}_2 \quad\; \text{OH} \end{array} \quad (II')$$

wherein R$^1$ and * are as indicated above, which is an enantiomer of the above ester, and treating the above ester (II) to remove the protecting group.

2. A process as claimed in claim 1, wherein the hydrolase is derived from a microorganism belonging to Pseudomonas or Chromobacterium.

3. A process as claimed in claim 1, wherein the hydrolase is a pig liver esterase.

4. A process as claimed in claim 1, wherein the racemate represented by the formula (I) is methyl 3-tert-butoxycarbonylaminobutanoate.

5. A process as claimed in claim 1, wherein the racemate represented by the formula (I) is butyl 3-tert-butoxycarbonylaminobutanoate.

6. A process as claimed in claim 1, wherein the racemate represented by the formula (I) is benzyl 3-tert-butoxycarbonylaminobutanoate.

* * * * *